United States Patent
Arlt et al.

(10) Patent No.: US 10,359,409 B2
(45) Date of Patent: Jul. 23, 2019

(54) METHOD FOR MEASURING A DEGREE OF HYDROGENATION

(71) Applicants: FRIEDRICH-ALEXANDER-UNIVERSITÄT ERLANGEN-NÜRNBERG, Erlangen (DE); HYDROGENIOUS TECHNOLOGIES GMBH, Erlangen (DE)

(72) Inventors: Wolfgang Arlt, Nürnberg (DE); Katharina Stark, Lichtenfels (DE); Peter Wasserscheid, Erlangen (DE)

(73) Assignees: FRIEDRICH-ALEXANDER-UNIVERSITÄT ERLANGEN-NÜRNBERG, Erlangen (DE); HYDROGENIOUS TECHNOLOGIES GMBH, Erlangen (DE)

( * ) Notice: Subject to any disclaimer, the term of this patent is extended or adjusted under 35 U.S.C. 154(b) by 139 days.

(21) Appl. No.: 15/525,713

(22) PCT Filed: Nov. 9, 2015

(86) PCT No.: PCT/EP2015/076056
§ 371 (c)(1),
(2) Date: May 10, 2017

(87) PCT Pub. No.: WO2016/075077
PCT Pub. Date: May 19, 2016

(65) Prior Publication Data
US 2017/0322192 A1 Nov. 9, 2017

(30) Foreign Application Priority Data
Nov. 10, 2014 (DE) .......... 10 2014 116 345

(51) Int. Cl.
*G01N 33/28* (2006.01)
*C01B 3/00* (2006.01)
(Continued)

(52) U.S. Cl.
CPC ....... *G01N 33/2829* (2013.01); *C01B 3/0015* (2013.01); *G01N 9/36* (2013.01);
(Continued)

(58) Field of Classification Search
CPC .......... G01N 9/36; G01N 29/02; G01N 33/22; G01N 2291/022
USPC ...................................... 73/61.41
See application file for complete search history.

(56) References Cited

U.S. PATENT DOCUMENTS 5,311,274 A * 5/1994 Cole, Jr. ........... G01N 33/03
356/128
2006/0226050 A1 10/2006 Gershtein et al.
(Continued)

FOREIGN PATENT DOCUMENTS

EP 1475349 A2 11/2004
EP 2042850 A2 4/2009

OTHER PUBLICATIONS

European Office Communication from EP Application No. EP 15794519.7, dated Apr. 16, 2018.
(Continued)

*Primary Examiner* — Benjamin R Schmitt
(74) *Attorney, Agent, or Firm* — Workman Nydegger

(57) ABSTRACT

A method for detecting a degree of hydrogenation of a liquid comprises one or more liquid hydrogen carriers, which can be hydrogenated, comprising: detecting a material property of the liquid and determining the degree of hydrogenation of the liquid on the basis of the detected material property of the liquid.

13 Claims, 3 Drawing Sheets

(51) Int. Cl.
    *G01N 29/024*     (2006.01)
    *G01N 9/36*     (2006.01)
    *G01N 33/22*     (2006.01)
    *G01N 21/41*     (2006.01)
    *G01N 21/45*     (2006.01)

(52) U.S. Cl.
    CPC ......... *G01N 21/4133* (2013.01); *G01N 21/45* (2013.01); *G01N 29/024* (2013.01); *G01N 33/22* (2013.01); *G01N 2291/02845* (2013.01); *Y02E 60/328* (2013.01)

(56) References Cited

U.S. PATENT DOCUMENTS

2007/0034532 A1     2/2007   Gershtein et al.
2008/0138674 A1     6/2008   Pez et al.

OTHER PUBLICATIONS

Papp et al., "Wasserstoff, Chemisch Gespeichert," Energie, vol. 62, Oct. 2014, pp. 963-969.
International Search Report for corresponding International PCT Application No. PCT/EP2015/076056, dated Feb. 2, 2016.
Brückner et al., "Evaluation of Industrially Applied Heat-Transfer Fluids as Liquid Organic Hydrogen Carrier Systems," ChemSusChem, vol. 7, 2014, pp. 229-235.
German Office Action from DE Application No. 102014116345.1, dated Jun. 1, 2015.
German Office Action from DE Application No. 102014116345.1, dated Feb. 15, 2018.

\* cited by examiner

METHOD FOR MEASURING A DEGREE OF HYDROGENATION

BACKGROUND

The present invention relates to a method and a measuring device for detecting a degree of hydrogenation of a liquid, which comprises one or more liquid hydrogen carriers which can be hydrogenated.

Document EP 1 475 349 describes organic hydrides as hydrogen stores.

Document EP 2 042 850 describes that the carbon content of a mixture can be determined by means of a density measurement and mixture-dependent variables. The density of an alkane increases with the molecular weight equal to the number of the carbon atoms. To detect materials other than alkanes in the mixture, a mixture variable different from the density is measured.

However, these documents do not describe how a physical material variable establishes a correlation to more than two components.

SUMMARY

The object on which the invention is based is to determine a degree of hydrogenation of a mixture of liquid hydrogen carriers in a simple manner.

According to a first aspect of the invention, the object is achieved by a method for detecting a degree of hydrogenation of a liquid, which comprises one or more liquid hydrogen carriers which can be hydrogenated, having the steps of detecting a material property of the liquid, and determining the degree of hydrogenation of the liquid on the basis of the detected material property of the liquid. The degree of hydrogenation is understood as the degree of saturation of the unbound electrons present in the starting state of the hydrogen carrier due to chemical bonding to hydrogen. In a hydrogen carrier which is not charged with hydrogen, having a maximum number of unbound electrons, the degree of hydrogenation is 0. In a hydrogen carrier which is completely charged with hydrogen, in which all double bonds are saturated by chemical bonding to hydrogen, and therefore a minimum number of unbound electrons is present in the hydrogen carrier, the degree of hydrogenation is 1.

The technical advantage is thus achieved, for example, that the degree of hydrogenation of a multicomponent system can be determined with the aid of only one thermophysical measured variable. In a multicomponent system, a mixture having at least two materials, it is generally difficult to carry out a unique concentration determination of the materials in the mixture using only one experimentally ascertained parameter. Surprisingly, in the multicomponent system of the present invention, which comprises a mixture of at least two materials, a unique function can be determined between the degree of hydrogenation of the liquid and a material property, for example, density or index of refraction. This is achieved in particular in that the materials have an identical chemical basic structure and no specific concentration determination of the materials in the mixture is carried out, but rather exclusively the degree of hydrogenation of the liquid is determined as a single uniform variable for the materials.

For example, in a multicomponent system according to the invention having two materials, the degree of hydrogenation can be indicated as a linear or a nonlinear, for example, exponential or polynomial, or as a logarithmic function of the index of refraction. The degree of hydrogenation of the material mixture can thus be uniquely determined with the aid of only one thermophysical measured variable, whereby rapid and effective detection of the degree of hydrogenation of one or multiple hydrogen carriers is enabled.

In one advantageous embodiment of the method, in the step of detecting the material property, at least one of the following material properties is detected: density, optical index of refraction, relative permittivity, speed of sound, viscosity, adsorption, absorption, or at least one material property which is derivable from material data such as density of the liquid.

The technical advantage is thus achieved, for example, that the mentioned material properties of the liquid enable an advantageous determination of the degree of hydrogenation of the multicomponent system, because a relationship, in particular a linear, a nonlinear, for example, an exponential or polynomial, or a logarithmic relationship exists between the mentioned material properties and the degree of hydrogenation of the material mixture. The material property of the adsorption of the liquid is understood as the adsorption capability of the liquid, or the adsorption capability of one or more liquid hydrogen carriers, which can be hydrogenated, of the liquid, on a solid surface. The material property of the absorption of the liquid is understood as the absorption capability of the liquid, or the absorption capability of one or more liquid hydrogen carriers, which can be hydrogenated, of the liquid, in the interior of a solid or a liquid.

In one advantageous embodiment of the method, the material property is an optical index of refraction, wherein the optical index of refraction is determined by means of a refractometer, a goniometer, or a Michelson interferometer.

The technical advantage is thus achieved, for example, that a precise detection of the index of refraction is performed, which can be carried out rapidly by the use of a refractometer, a goniometer, or a Michelson interferometer, and can optionally also run automatically. The determination of the index of refraction by means of refractometer, goniometer, or Michelson interferometer is additionally possible with high accuracy, whereby an advantageous determination of the degree of hydrogenation of the hydrogen carriers is ensured.

In a further advantageous embodiment of the method, the method comprises the steps of detecting the density of the liquid and determining the degree of hydrogenation on the basis of the density of the liquid.

The technical advantage is thus achieved, for example, that the accuracy of the method is increased by the additional detection of the density of the liquid. If, in addition to the detected material property of the liquid, the density of the liquid is also detected, two experimentally determined parameters are available to determine the degree of hydrogenation of the multicomponent mixture according to the invention. The accuracy of the detection can thus be increased and the degree of hydrogenation of the hydrogen carriers can advantageously be determined.

In a further advantageous embodiment of the method, the liquid comprises a mixture of an unsaturated cyclic hydrocarbon compound and an at least partially hydrogenated unsaturated cyclic hydrocarbon compound, and preferably comprises a mixture of N-ethyl carbazole and at least partially hydrogenated N-ethyl carbazole, or a mixture of dibenzyl toluene and at least partially hydrogenated dibenzyl toluene, or a mixture of benzyl toluene and at least partially hydrogenated benzyl toluene, or a mixture of benzyl toluene, dibenzyl toluene, at least partially hydrogenated dibenzyl toluene, and at least partially hydrogenated benzyl toluene.

The technical advantage is thus achieved, for example, that particularly efficient hydrogen carriers can be selected by way of the mentioned compounds. In unsaturated cyclic hydrocarbon compounds, a variety of unsaturated carbon-carbon double bonds is available, which can react with hydrogen molecules to form saturated carbon-carbon double bonds, whereby hydrogen can be stored. For example, a ((5-methyl-1,3-phenylene)bis(methylene) dibenzene molecule has nine unsaturated carbon-carbon double bonds, which can absorb nine hydrogen molecules in the scope of complete hydrogenation by hydrogen. Due to the high ratio of stored hydrogen molecules per cyclic hydrocarbon compound, effective hydrogen storage can be enabled in a limited volume of liquid.

An unsaturated cyclic hydrocarbon compound comprises any hydrocarbon compound which comprises at least one hydrocarbon ring, and which comprises at least one carbon-carbon double bond. The unsaturated cyclic hydrocarbon compound can comprise an aromatic or nonaromatic cyclic hydrocarbon compound. The unsaturated cyclic hydrocarbon compound can comprise a hydrocarbon compound having one or more hydrocarbon rings, wherein in the event of a plurality of hydrocarbon rings, the hydrocarbon rings can comprise annelated hydrocarbon rings or hydrocarbon rings bonded by substituents.

In the unsaturated cyclic hydrocarbon compound, at least one carbon atom can be replaced by a heteroatom comprising oxygen, sulfur, or nitrogen. Each carbon atom or heteroatom of the unsaturated cyclic hydrogen compound can be substituted with the substituent which is selected from the group consisting of methyl, ethyl, propyl, butyl, chlorine, fluorine, or bromine.

An at least partially hydrogenated unsaturated cyclic hydrocarbon compound comprises a cyclic hydrocarbon compound, in which at least one carbon-carbon double bond of the cyclic hydrocarbon compound is replaced by a carbon-carbon single bond. An at least partially hydrogenated unsaturated cyclic hydrocarbon compound preferably comprises a completely hydrogenated cyclic hydrocarbon compound, in which all carbon-carbon double bonds of the cyclic hydrocarbon compound are replaced by carbon-carbon single bonds.

The mixture of an unsaturated cyclic hydrocarbon compound and an at least partially hydrogenated unsaturated cyclic hydrocarbon compound can comprise various partially hydrogenated unsaturated cyclic hydrocarbon compounds with various degrees of hydration of the unsaturated cyclic hydrocarbon compounds.

The terms N-ethyl carbazole, benzyl toluene, and dibenzyl toluene additionally preferably comprise each constitutional isomer and each stereoisomer of the mentioned compounds.

An at least partially hydrogenated N-ethyl carbazole comprises any N-ethyl carbazole compound in which at least one carbon-carbon double bond of the N-ethyl carbazole is replaced by a carbon-carbon single bond, and preferably all carbon-carbon double bonds are replaced by carbon-carbon single bonds.

An at least partially hydrogenated dibenzyl toluene comprises any dibenzyl toluene compound in which at least one carbon-carbon double bond of the dibenzyl toluene is replaced by a carbon-carbon single bond, and preferably all carbon-carbon double bonds are replaced by carbon-carbon single bonds.

An at least partially hydrogenated benzyl toluene comprises any benzyl toluene compound in which the at least one carbon-carbon double bond of the benzyl toluene is replaced by a carbon-carbon single bond, and preferably all carbon-carbon double bonds are replaced by carbon-carbon single bonds.

An at least partially hydrogenated N-ethyl carbazole preferably comprises 9-ethyl-2,3,4,9-tetrahydro-1H-carbazole, 9-ethyl-2,3,4,5,6,9-hexahydro-1H-carbazole, 9-ethyl-2,3,4,4a,5,6,7,8,9,9a-decahydro-1H-carbazole, 9-ethyl-2,3,4,5,6,7,8,9-octahydro-1H-carbazole, or 9-ethyldodecahydro-1H-carbazole.

An at least partially hydrogenated dibenzyl toluene preferably comprises 1-benzyl-3-(cyclohexylmethyl)-5-methyl benzene, ((5-methyl-1,3-phenylene)bis(methylene) dicyclohexane, ((5-methylcyclohexane-1,3-diyl)bis(methylene) dicyclohexane, ((5-methyl-1,3-phenylene)bis(methylene) dibenzene, 1-benzyl-4-(cyclohexylmethyl)-2-methyl benzene, ((2-methyl-1,4-phenylene)bis(methylene) dicyclohexane, ((2-methylcyclohexane-1,4-diyl)bis(methylene) dicyclohexane, ((2-methyl-1,4-phenylene)bis(methylene) dibenzene, 2-benzyl-4-(cyclohexylmethyl)-1-methyl benzene, ((4-methyl-1,3-phenylene)bis(methylene) dicyclohexane, ((4-methylcyclohexane-1,3-diyl)bis(methylene) dicyclohexane, ((4-methyl-1,3-phenylene)bis(methylene) dibenzene, 1-benzyl-3-(cyclohexylmethyl)-2-methyl benzene, ((2-methyl-1,3-phenylene)bis(methylene) dicyclohexane, ((2-methylcyclohexane-1,3-diyl)bis(methylene) dicyclohexane, ((2-methyl-1,3-phenylene)bis(methylene) dibenzene, 1-benzyl-2-(cyclohexylmethyl)-4-methyl benzene, ((4-methyl-1,2-phenylene)bis(methylene) dicyclohexane, ((4-methylcyclohexane-1,2-diyl)bis(methylene) dicyclohexane, or ((4-methyl-1,2-phenylene)bis(methylene) dibenzene.

In a further advantageous embodiment of the method, the degree of hydrogenation of the liquid is determined on the basis of a linear relationship of the degree of hydrogenation and the detected material property.

The technical advantage is thus achieved, for example, that the degree of hydrogenation can be calculated in a simple and rapid manner, and thus an efficient and automated determination of the degree of hydrogenation of the liquid, for example, in a tank, can be achieved.

In a further advantageous embodiment of the method, the degree of hydrogenation of the liquid is determined on the basis of a nonlinear or logarithmic relationship of the degree of hydrogenation and the detected material property.

The technical advantage is thus achieved, for example, that the degree of hydrogenation can be calculated in an advantageous manner. A nonlinear relationship can comprise, for example, an exponential or polynomial relationship. Due to the nonlinear and/or logarithmic relationship between the detected material property and the degree of hydrogenation, the degree of hydrogenation of the material mixture can be uniquely determined with the aid of only one thermophysical measured variable. Due to the advantageous calculation of the degree of hydrogenation, efficient and automated determination of the degree of hydrogenation of the liquid, for example, in a tank, can be achieved.

In one advantageous embodiment of the method, the material property, in particular density, is determined by means of a hydrometer, a pycnometer, a hydrostatic weighing, or an oscillation measurement. The technical advantage is thus achieved, for example, that an accurate detection of the material property, in particular density, is performed. A measurement of the degree of hydrogenation of the liquid is therefore furthermore possible in the laboratory and also in technical embodiments, wherein the material property of the liquid, in particular density, can be determined with a high precision.

According to a second aspect of the invention, the object is achieved by a measuring device for detecting a degree of hydrogenation of a liquid, which comprises one or more liquid hydrogen carriers which can be hydrogenated, having a detection device for detecting a material property of the liquid; and a determination device for determining the degree of hydrogenation on the basis of the detected material property of the liquid. The technical advantage is thus also achieved, for example, that the degree of hydrogenation of a multicomponent system can be determined with the aid of only one thermophysical measured variable.

In one advantageous embodiment of the measuring device, the detection device is configured to detect at least one of the following material properties: density, optical index of refraction, relative permittivity, speed of sound, viscosity, adsorption, absorption, or at least one material property which is derivable from material data such as density of the liquid.

The technical advantage is thus achieved, for example, that the mentioned material properties of the liquid enable an advantageous determination of the degree of hydrogenation of the multicomponent system.

In one advantageous embodiment of the measuring device, the material property is an optical index of refraction, wherein the detection device comprises a refractometer, a goniometer, or a Michelson interferometer. Thus, for example, the technical advantage is achieved that the index of refraction can be ascertained with a high precision.

In a further advantageous embodiment of the measuring device, the measuring device comprises a detection device for detecting data of the liquid in a tank, in particular weight or volume. The technical advantage is thus achieved, for example, that the quantity of the liquid can be used for further calculations. Efficient and accurate determination of the degree of hydrogenation of the liquid in the tank can thus be carried out.

In a further advantageous embodiment of the measuring device, the measuring device comprises a calculation device for calculating a stored or storable quantity of energy in the tank on the basis of the degree of hydrogenation and the quantity of the liquid. The technical advantage is thus achieved, for example, that the energy content of the tank can be displayed to a user, whereby the user can better estimate the remaining energy content of the liquid in the tank.

In one advantageous embodiment of the measuring device, the measuring device comprises a fuel gauge to display the stored or storable quantity of energy in the tank. The technical advantage is thus achieved, for example, that by way of the fuel gauge, in the event of a known energy consumption of the tank in a certain time interval, for example, in the event of a consistent hydrogen consumption of a tank of a vehicle, a prognosis and display of the remaining quantity of energy, or remaining quantity of hydrogen, of the tank is possible by way of the fuel gauge. Thus, for example, in a vehicle which consumes hydrogen, the remaining quantity of energy of the tank, or the remaining range of the automobile, can be ascertained and displayed by the fuel gauge.

In one advantageous embodiment of the measuring device, the detection device comprises a hydrometer, a pycnometer, a hydrostatic scale, or a device for oscillation measurement, in particular a flexural resonator. The technical advantage is thus achieved, for example, that the density can be determined with a high precision.

According to a third aspect of the invention, the object is achieved by a vehicle having a tank for a liquid, which comprises one or more liquid hydrogen carriers which can be hydrogenated, having the measuring device according to the second aspect. The technical advantage is thus achieved, for example, that the measuring device can be used for a fuel gauge for the vehicle.

BRIEF DESCRIPTION OF THE DRAWINGS

Exemplary embodiments of the invention are illustrated in the drawings and will be described in greater detail hereafter.

In the figures.

DETAILED DESCRIPTION OF VARIOUS EMBODIMENTS

Figure 1:
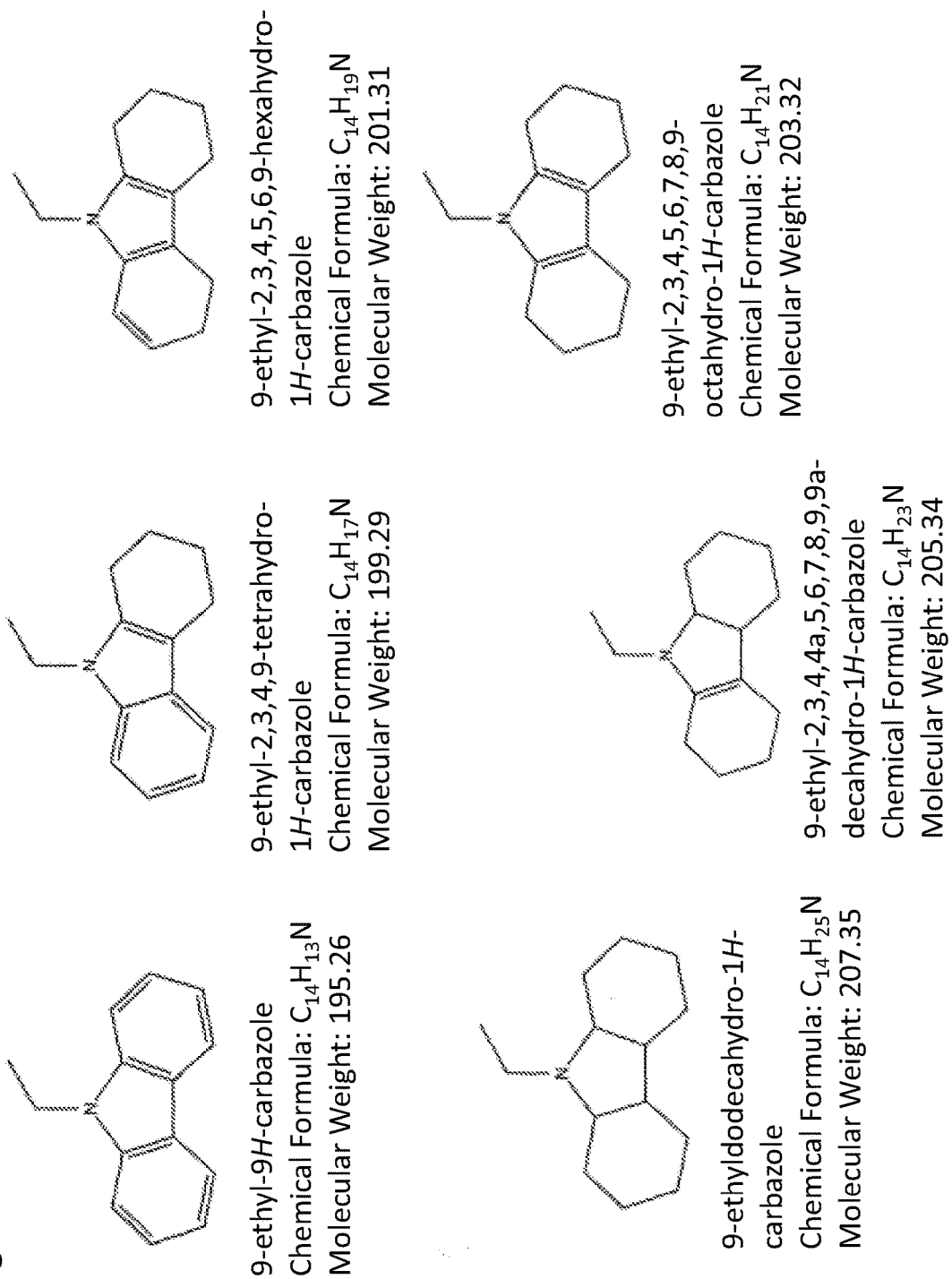
FIG. 1 shows partially hydrogenated isomers of N-ethyl carbazole.
Figure 2:
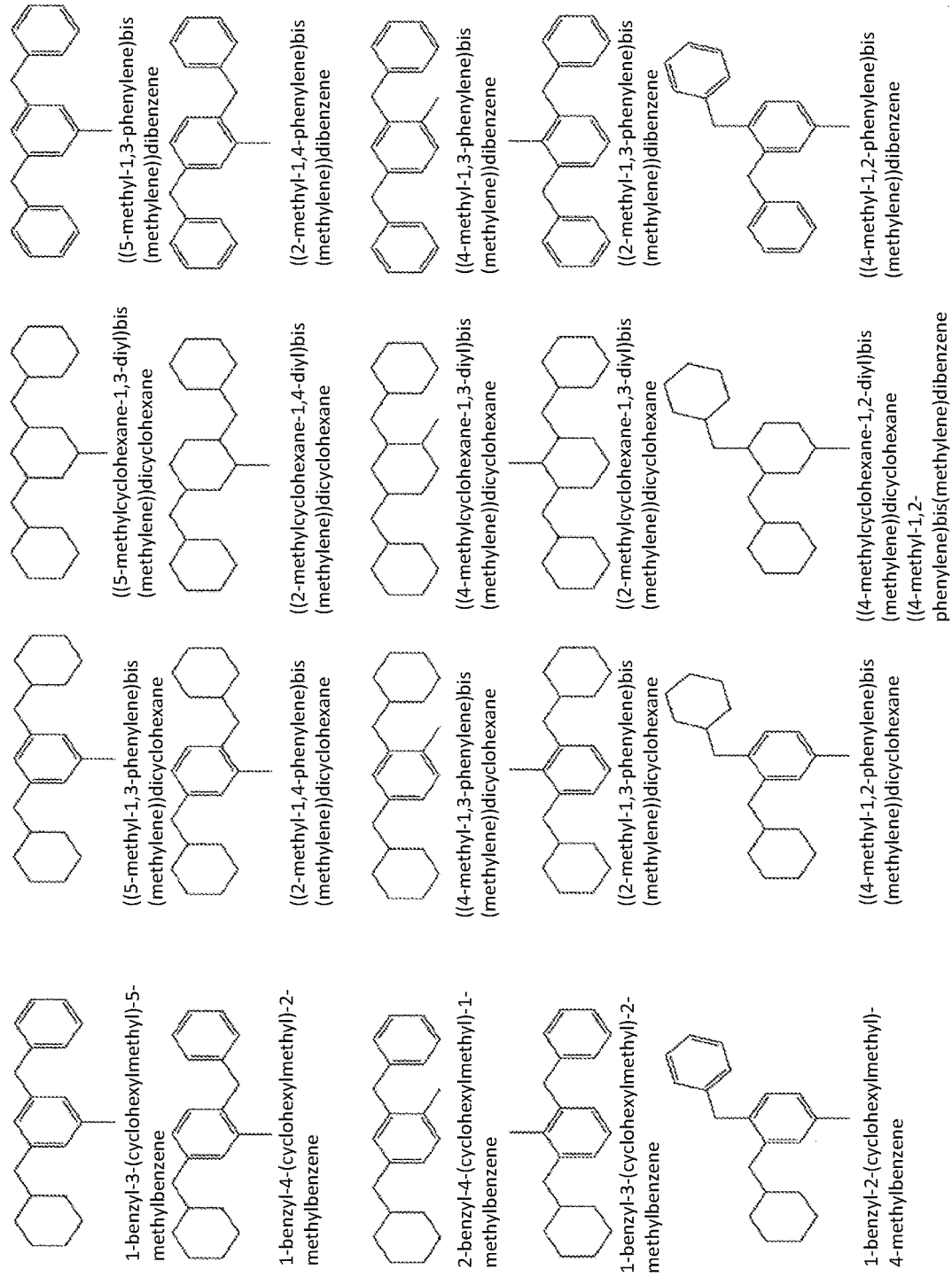
FIG. 2 shows isomers of dibenzyl toluene.

FIG. 1 shows partially hydrogenated isomers of N-ethyl carbazole and FIG. 2 shows possible isomers of dibenzyl toluene. Both substances are examples of a liquid hydrogen carrier (LOHC—Liquid Organic Hydrogen Carrier), which comprises aromatic compounds.

A low-energy form of the liquid hydrogen carrier is reversibly converted by means of catalyzed hydrogenation by hydrogen into a high-energy form. In a back reaction, which is differently catalyzed, for example, by temperature increase and/or reduction of the hydrogen pressure, hydrogen is reclaimed again from the hydrogenated high-energy form while forming the low-energy form. The reaction is reversible, so that the liquid hydrogen carrier can be guided from a low-energy to a high-energy location in the circuit, without consuming itself. The liquid hydrogen carrier is the transporter for energy in the form of hydrogen.

Particularly advantageously usable liquid hydrogen carriers enable this reversible conversion under technically relevant conditions, for example, at pressures and temperatures which are easily technically feasible. The hydrogen storage in liquid hydrogen carriers has the advantage that the liquid hydrogen carriers are liquid under the process conditions used, are unpressurized in the storage, and have a high similarity to conventional liquid fuels in the physicochemical properties thereof. Therefore, pumps for the transport and containers for the storage from the field of fuel and combustible material logistics can be used. The hydrogen storage in chemically bound form in an organic liquid enables unpressurized storage at normal conditions over long periods of time without significant hydrogen loss. Liquid hydrogen carriers are based, for example, on the materials N-ethyl carbazole, benzyl toluene, or dibenzyl toluene.

Due to the different isomers, more than two materials can arise during the hydrogenation or dehydrogenation procedure and can be present simultaneously in a complex mixture. The liquid which is formed by the liquid hydrogen carrier therefore comprises a number of partially hydrogenated, fully hydrogenated, or non-hydrogenated components in different concentrations.

Because a liquid hydrogen carrier is not consumed during the use as a hydrogen energy supplier, the liquid formed by the hydrogen carrier is not removed from a tank, but rather only changes the energy content thereof due to the changing concentrations of the individual components. A material pair of a hydrogen-charged and hydrogen-discharged form of the liquid hydrogen carrier is therefore always located in the tank.

A determination of the degree of hydrogenation h in this multicomponent mixture could be performed in that the respective individual concentrations are measured. However, this method is complex. In a simpler manner, the thermophysical variables such as density ρ and index of refraction n of the liquid may be used to determine a degree of hydrogenation h.

The index of refraction n is a dimensionless physical variable. The index of refraction n specifies the ratio of the speed of light in vacuum to the propagation speed of light in the liquid. Therefore, the index of refraction in vacuum is equal to 1 and increases with increasing density. In the specification, the wavelength of the measuring light should be noted. The density ρ of the liquid is the mass of the liquid divided by its volume, for example, in kilograms per cubic meter. In general, these variables are correlated with one another.

The permittivity or dielectric conductivity describes the permeability of a material or material mixture to electric fields. The relative permittivity $\Box_r$ is defined as the dimensionless ratio of the permittivity in material and in vacuum. The latter is referred to as the field constant. Instead of the field constant, the permittivity of air is often also used as the reference variable.

The relative permittivity of a material or material mixture, for example, a liquid, can be determined with the aid of a capacitor. The capacitance of the capacitor, filled using the material or the material mixture having unknown permittivity, is determined using an LCR meter. The capacitance of the same capacitor filled using a substance of known permittivity, generally air, is used as a reference. The ratio of the two capacitances is referred to as the relative permittivity.

The dynamic viscosity is a measure of the viscosity of a liquid or a gas. The fluidity of a material decreases with increasing dynamic viscosity.

The use of the index of refraction n and/or the density ρ to determine the degree of hydrogenation h is advantageous in particular with liquid hydrogen carriers if non-hydrogenated, partially hydrogenated, and fully hydrogenated forms of the hydrogen carrier are stored in a mixture together in a tank.

In a multicomponent mixture, which consists of materials having identical basic structure, the degree of hydrogenation is a linear function of the index of refraction n and/or the density ρ. A simple and efficient determination of the degree of hydrogenation of the hydrogen-storing liquid can thus be ensured on the basis of a measurement of the index of refraction n and/or the density ρ.

In a further embodiment, the degree of hydrogenation can be a nonlinear or a logarithmic function of the index of refraction n and/or the density ρ. A nonlinear relationship can comprise, for example, an exponential or a polynomial relationship. Because the degree of hydrogenation can be a nonlinear or a logarithmic function of the index of refraction n and/or the density ρ, a simple and efficient determination of the degree of hydrogenation is enabled. Due to the advantageous calculation of the degree of hydrogenation, an automated determination of the degree of hydrogenation of the liquid, for example, in a tank, can be achieved.

Figure 3:
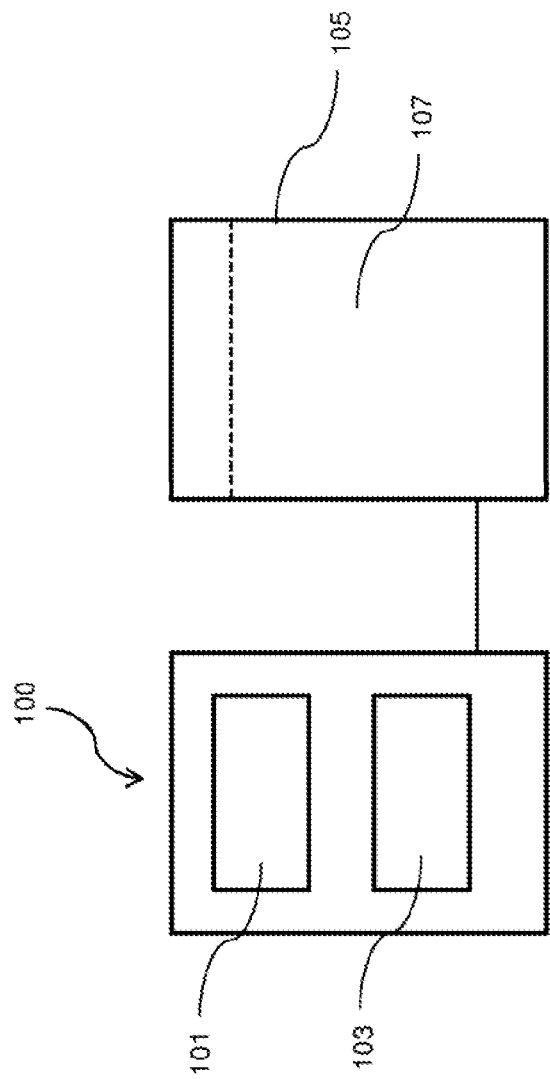
FIG. 3 shows a schematic view of a measuring device for detecting a degree of hydrogenation of a liquid.

FIG. 3 shows a schematic view of a measuring device 100 for detecting a degree of hydrogenation. The measuring device 100 comprises a detection device 101 for detecting a material property of the liquid 107, for example, the optical index of refraction of the liquid 107 or a density detection device 101 for detecting the density of the liquid 107. Furthermore, the detection device 100 comprises a determination device 103 for determining the degree of hydrogenation on the basis of the detected material property of the liquid 107, for example, the optical index of refraction or the density of the liquid 107. Both thermophysical measured variables can be measured in a simple manner. The determination device 103 can be formed, for example, by a processor having a memory, which permits the execution of mathematical operations.

The measuring device 100 can be used in this case as a fuel gauge, which displays how high the degree of hydrogenation of the liquid 107 in the tank 105 is. The fuel gauge can be attached to the tank 105 itself or installed in supply lines and/or drain lines to the tank 105. The tank contents can be recirculated through these lines for better mixing. The measuring device 100 can be used in stationary or mobile tanks 105 for the liquid hydrogen carriers. The quantity of a liquid hydrogen carrier in kilograms which is located in the tank 105 is known, for example, by weighing upon filling.

In the stationary case, the measuring device 100 can display how much energy in the form of releasable hydrogen is contained in the tank 105 and can display the energy content of the tank 105. Conclusions can be drawn therefrom about a chronological range of the tank 105. A user of the tank 105 for liquid hydrogen carriers can ascertain in this manner what quantity of energy is storable in the tank 105.

The measuring device 105 can additionally be used to track the hydrogenation of a liquid hydrogen carrier in a reactor, so that a chemical conversion can be determined. The measuring device 100 can be used to monitor the reaction progress in chemical reactors, which store hydrogen in liquid hydrogen carriers or generate hydrogen from the hydrogen carriers.

The measuring device 100 can be used to display the range of a vehicle, which comprises a tank 105 for liquid hydrogen carriers, if the energy requirement per kilometer of driving performance is known. The range is directly linked to the energy content, which is based on the quantity of the liquid hydrogen carrier and the degree of hydrogenation h.

The vehicle uses the released hydrogen for the drive. For this purpose, a change of the high-energy form of the liquid hydrogen carrier into a low-energy form while forming hydrogen is provided. If the vehicle has a single tank 105 for the liquid hydrogen carriers, a mixture of hydrogenated liquid hydrogen carriers is provided in this tank 105. The measuring device 100 can be used by difference calculation to account for the energy supply at a filling station, if a partially hydrogenated or non-hydrogenated liquid hydrogen carrier is discharged at the filling station and subsequently a partially hydrogenated or fully hydrogenated liquid hydrogen carrier is acquired from the filling station.

All features which are explained and shown in conjunction with individual embodiments of the invention can be provided in different combinations in the subject matter according to the invention, to implement the advantageous effects thereof simultaneously.

The scope of protection of the present invention is given by the claims and is not restricted by the features which are explained in the description or shown in the figures.

LIST OF REFERENCE SIGNS 100 measuring device
101 detection device/density detection device
103 determination device
105 tank 107 liquid
S101 method step
S102 method step
S201 method step
S202 method step

The invention claimed is:

1. A method for detecting a degree of hydrogenation of a liquid, which comprises one or more liquid hydrogen carriers which can be hydrogenated, having the following steps:
  detecting a material property of the liquid; and
  determining the degree of hydrogenation of the liquid on the basis of the detected material property of the liquid;
  wherein the liquid comprises a mixture of dibenzyl toluene and at least partially hydrogenated dibenzyl toluene, or a mixture of benzyl toluene and at least partially hydrogenated benzyl toluene, or a mixture of benzyl toluene, dibenzyl toluene, at least partially hydrogenated dibenzyl toluene, and at least partially hydrogenated benzyl toluene; and
  wherein the degree of hydrogenation of the liquid is determined on the basis of a linear relationship of the degree of hydrogenation and the detected material property.

2. The method as claimed in claim 1, wherein in the step of detecting the material property, at least one of the following material properties is detected: density, optical index of refraction, relative permittivity, speed of sound, viscosity, adsorption, or absorption.

3. The method as claimed in claim 2, wherein the density is determined by means of a hydrometer, a pycnometer, a hydrostatic weighing, or an oscillation measurement.

4. The method as claimed in claim 1, wherein the material property is an optical index of refraction, and wherein the optical index of refraction is determined by means of a refractometer, a goniometer, or a Michelson interferometer.

5. The method as claimed in claim 1, furthermore having the steps of detecting the density of the liquid and determining the degree of hydrogenation based on the density of the liquid.

6. A measuring device for detecting a degree of hydrogenation of a liquid, which comprises one or more liquid hydrogen carriers which can be hydrogenated, having:
  a detection device for detecting a material property of the liquid; and
  a determination device for determining the degree of hydrogenation on the basis of the detected material property of the liquid;
  wherein the liquid comprises a mixture of dibenzyl toluene and at least partially hydrogenated dibenzyl toluene, or a mixture of benzyl toluene and at least partially hydrogenated benzyl toluene, or a mixture of benzyl toluene, dibenzyl toluene, at least partially hydrogenated dibenzyl toluene, and at least partially hydrogenated benzyl toluene; and
  wherein the degree of hydrogenation of the liquid is determined on the basis of a linear relationship of the degree of hydrogenation and the detected material property.

7. The measuring device as claimed in claim 6, wherein the detection device is configured to detect at least one of the following material properties: density, optical index of refraction, relative permittivity, speed of sound, viscosity, adsorption, or absorption.

8. The measuring device as claimed in claim 6, wherein the material property is an optical index of refraction, and wherein the detection device comprises a refractometer, a goniometer, or a Michelson interferometer.

9. The measuring device as claimed in claim 6, wherein the measuring device comprises a detection device for detecting weight or volume of the liquid in a tank.

10. The measuring device as claimed in claim 9, wherein the measuring device comprises a calculation device for calculating a stored or storable quantity of energy in the tank on the basis of the degree of hydrogenation and the quantity of liquid.

11. The measuring device as claimed in claim 10, wherein the measuring device comprises a fuel gauge for displaying the stored or storable quantity of energy in the tank.

12. The measuring device as claimed in claim 9, wherein the detection device comprises a hydrometer, a pycnometer, a hydrostatic scale, or a device for oscillation measurement.

13. A vehicle having a tank for a liquid, which comprises one or more liquid hydrogen carriers which can be hydrogenated, having the measuring device as claimed in claim 6.

* * * * *